US010337969B2

(12) United States Patent
Safai et al.

(10) Patent No.: US 10,337,969 B2
(45) Date of Patent: Jul. 2, 2019

(54) HIGH SPEED VACUUM CYCLING EXCITATION SYSTEM FOR OPTICAL INSPECTION SYSTEMS

(71) Applicant: The Boeing Company, Chicago, IL (US)

(72) Inventors: Morteza Safai, Newcastle, WA (US); Xiaoxi Wang, Seattle, WA (US)

(73) Assignee: THE BOEING COMPANY, Chicago, IL (US)

(*) Notice: Subject to any disclaimer, the term of this patent is extended or adjusted under 35 U.S.C. 154(b) by 136 days.

(21) Appl. No.: 15/629,673

(22) Filed: Jun. 21, 2017

(65) Prior Publication Data
US 2018/0372603 A1 Dec. 27, 2018

(51) Int. Cl.
G01N 3/32 (2006.01)
G01N 3/24 (2006.01)
G01B 11/16 (2006.01)
G01N 3/60 (2006.01)
G01N 19/04 (2006.01)

(52) U.S. Cl.
CPC ............ G01N 3/24 (2013.01); G01B 11/162 (2013.01); G01N 3/32 (2013.01); G01N 3/60 (2013.01); G01N 19/04 (2013.01); G01N 2203/0007 (2013.01); G01N 2203/0208 (2013.01); G01N 2203/0417 (2013.01)

(58) Field of Classification Search
CPC ............... G01N 3/00; G01N 3/24; G01N 3/32
See application file for complete search history.

(56) References Cited

U.S. PATENT DOCUMENTS 5,257,088 A 10/1993 Tyson, II et al.
5,481,356 A 1/1996 Pouet et al.
5,786,533 A 7/1998 Newman
6,246,483 B1 6/2001 Smith et al.
6,717,681 B1 4/2004 Bard et al.
(Continued)

FOREIGN PATENT DOCUMENTS

EP 1061322 A2 12/2000
EP 2523064 A2 11/2012
(Continued)

OTHER PUBLICATIONS

Burleigh, D., et al., "Laser Shearographic Testing of Foam Insulation on Cryogenic Fuel Tanks", Review of Progress in Quantitative Nondestructive Evaluation, vol. 12, 1993, pp. 411-418.
(Continued)

Primary Examiner — Nguyen Q. Ha
(74) Attorney, Agent, or Firm — MH2 Technology Law Group LLP

(57) ABSTRACT

A vacuum system and method for inspecting a workpiece that can include use of the vacuum system, where the vacuum system can include a housing defining at least a portion of a vacuum chamber, a piston within the housing that oscillates to vary a volume of the vacuum chamber, a first valve and a second valve in fluid communication with the vacuum chamber, and a hood in fluid communication with the second valve and the vacuum chamber. The vacuum system can include high-speed valves that enable vacuum system cycling and thus vacuum pressure cycling at a rapid frequency.

22 Claims, 6 Drawing Sheets

(56) References Cited

U.S. PATENT DOCUMENTS

| | | |
|---|---|---|
| 6,924,888 B2 | 8/2005 | Steinbichler et al. |
| 2001/0040682 A1 | 11/2001 | Lindsay et al. |
| 2004/0212795 A1 | 10/2004 | Steinbichler et al. |
| 2005/0264796 A1 | 12/2005 | Shaw et al. |
| 2008/0295579 A1 | 12/2008 | Safai et al. |
| 2013/0114088 A1 | 5/2013 | Newman |
| 2014/0033799 A1* | 2/2014 | Newman .................. G01B 9/02 73/37 |
| 2015/0215584 A1* | 7/2015 | Tapia ................. G01N 21/8851 348/125 |
| 2016/0209205 A1 | 7/2016 | Enevoldsen et al. |

FOREIGN PATENT DOCUMENTS

| | | | |
|---|---|---|---|
| JP | 04351936 A * | 12/1992 | ............ G01M 19/00 |
| WO | 2006/001712 A2 | 1/2006 | |

OTHER PUBLICATIONS

Davis, C. et al., "Shearographic Non-Destructive Evaluation of Space Shuttle Thermal Protection Systems", 1995, 12 pages.

Lee, J. et al., "Application of grating shearography and speckle shearography to mechanical analysis of composite material", Composites: Part A, vol. 35, 2004, pp. 965-976.

Joenathan, C. et al., "Speckle interferometry with temporal phase evaluation for measuring large-object deformation", Applied Optics, vol. 37, No. 13, May 1, 1998, pp. 2608-2614.

Unknown, "High-Speed Dispensing Valve", TLX Technologies: Innovative Electromagnetic Solutions, 2008, 1 page.

Specification and drawings in co-pending U.S. Appl. No. 15/629,638, 30 pages.

Extended European Search Report dated Nov. 6, 2018 in corresponding European Application No. 18178462.0 (9 pages).

Extended European Search Report dated Nov. 2, 2018 in related corresponding European Application No. 18178451.3, 13 pages.

* cited by examiner

HIGH SPEED VACUUM CYCLING EXCITATION SYSTEM FOR OPTICAL INSPECTION SYSTEMS

TECHNICAL FIELD

The present teachings relate to testing, inspection, and metrology, and more particularly to a vacuum system and method that can be used for testing, inspection, metrology, as well as other uses.

BACKGROUND

Vacuum systems are commonly used in industry for testing, inspection, and metrology. A vacuum system can be used, for example, to assess whether a product design and/or a manufacturing process is sufficient to ensure that the product conforms to standards of load or stress resistance. In another use, a product surface can be exposed to cyclic loading from a vacuum to test a resistance of the product to fatigue. During destructive testing, resistance to a vacuum stress can be measured using an increasing vacuum applied to a product until the product fails. During non-destructive testing or inspection, stresses can be applied to some or all articles from a production lot using a vacuum system to ensure that the articles have been properly manufactured.

A vacuum system that allows testing modes and conditions not available with conventional system designs would be a welcome addition to the art.

SUMMARY

The following presents a simplified summary in order to provide a basic understanding of some aspects of one or more implementations of the present teachings. This summary is not an extensive overview, nor is it intended to identify key or critical elements of the present teachings, nor to delineate the scope of the disclosure. Rather, its primary purpose is merely to present one or more concepts in simplified form as a prelude to the detailed description presented later.

In one implementation of the present teachings, a vacuum system for inspecting a workpiece includes a housing defining at least a portion of a vacuum chamber, a piston within the housing, wherein the piston is configured to oscillate, thereby varying a chamber volume of the vacuum chamber, a first valve in fluid communication with the vacuum chamber, wherein the first valve includes a first or open position that permits an intake of a gas into the vacuum chamber and an exhaust of the gas out of the vacuum chamber, and a second closed position that prevents the intake of the gas into the vacuum chamber and the exhaust of the gas out of the vacuum chamber through the first valve, a second valve in fluid communication with the vacuum chamber, wherein the second valve includes an open position that permits the intake of the gas into the vacuum chamber and the exhaust of the gas out of the vacuum chamber, and a closed position that prevents the intake of the gas into the vacuum chamber and the exhaust of the gas out of the vacuum chamber through the second valve, and a hood in fluid communication with the second valve and the vacuum chamber, wherein the second valve, in the open position, permits a flow of the gas between the vacuum chamber and the hood and, in the closed position, prevents the flow of the gas between the vacuum chamber and the hood through the second valve.

In this implementation, the hood can be configured to be positioned on a surface the workpiece during an application of a vacuum force to the surface of the workpiece by the vacuum system during the inspecting. The vacuum system can further include a laser configured to activate and deactivate during inspection of the workpiece wherein, during the activation, the laser emits a laser beam which illuminates the surface of the workpiece. Further, the vacuum system can include a camera configured to image the surface of the workpiece during the inspection of the workpiece.

In an implementation, at least one of the first valve and the second valve can be a solenoid pneumatic valve. Further, the piston can be configured to move from a first position in which the chamber volume is a maximum chamber volume, to a second position in which the chamber volume is a minimum chamber volume, and back to the first position at a frequency range of from 0.1 hertz to 1000 hertz. The vacuum system can further include a driver chamber defined at least in part by the housing and a driver coupled to the piston, positioned within the driver chamber, and configured to oscillate the piston, wherein the piston separates the driver chamber from the vacuum chamber.

In another implementation of the present teachings, shearography system for inspecting a workpiece includes a vacuum system. The vacuum system includes a housing defining at least a portion of a vacuum chamber, a piston within the housing, wherein the piston is configured to oscillate, thereby varying a chamber volume of the vacuum chamber, a first solenoid pneumatic valve in fluid communication with the vacuum chamber, wherein the first solenoid pneumatic valve includes a first or open position that permits an intake of a gas into the vacuum chamber and an exhaust of the gas out of the vacuum chamber, and a second closed position that prevents the intake of the gas into the vacuum chamber and the exhaust of the gas out of the vacuum chamber through the first solenoid pneumatic valve, a second solenoid pneumatic valve in fluid communication with the vacuum chamber, wherein the second solenoid pneumatic valve includes an open position that permits the intake of the gas into the vacuum chamber and the exhaust of the gas out of the vacuum chamber, and a closed position that prevents the intake of the gas into the vacuum chamber and the exhaust of the gas out of the vacuum chamber through the second solenoid pneumatic valve, and a hood in fluid communication with the second solenoid pneumatic valve and the vacuum chamber, wherein the second solenoid pneumatic valve, in the open position, permits a flow of the gas between the vacuum chamber and the hood and, in the closed position, prevents the flow of the gas between the vacuum chamber and the hood through the second solenoid pneumatic valve. The shearography system further includes a laser configured to activate and deactivate during inspecting of the workpiece wherein, during the activation, the laser emits a laser beam which illuminates the workpiece, a camera configured to image the workpiece during inspecting of the workpiece, and a controller configured to coordinate operation of the vacuum system, the laser, and the camera during inspecting of the workpiece.

In this implementation, the piston can be configured to move from a first position in which the chamber volume is a maximum chamber volume, to a second position in which the chamber volume is a minimum chamber volume, and back to the first position at a frequency range of from 0.1 hertz to 1000 hertz. Further, the controller can be configured to coordinate operation of the piston during inspecting of the workpiece. The shearography system can also include a driver chamber defined at least in part by the housing and a driver coupled to the piston, positioned within the driver chamber, and configured to oscillate the piston, wherein the piston separates the driver chamber from the vacuum chamber.

In another implementation, a method for inspecting a workpiece includes obtaining a first image of a surface of the workpiece at atmospheric pressure, increasing a vacuum pressure applied to the surface of the workpiece from the atmospheric pressure to a first vacuum pressure using a vacuum system, obtaining a second image of the surface of the workpiece at the first vacuum pressure, decreasing the vacuum pressure applied to the surface of the workpiece from the first vacuum pressure to a second vacuum pressure that is lower than the first vacuum pressure and higher than the atmospheric pressure without decreasing the vacuum pressure to the atmospheric pressure, obtaining a third image of the surface of the workpiece at the second vacuum pressure, and increasing the vacuum pressure applied to the surface of the workpiece from the second vacuum pressure to a third vacuum pressure that is higher than the first vacuum pressure without decreasing the vacuum pressure to the atmospheric pressure.

In this implementation of the present teachings, the first image is a first reference image and the method further includes illuminating the surface of the workpiece using a laser beam output by a laser while the first vacuum pressure is applied to the surface, performing the obtaining of the second image while the surface is illuminated with the laser beam, wherein the second image is a first inspection image of the surface, illuminating the surface using the laser beam while the second vacuum pressure is applied to the surface, and performing the obtaining of the third image while the surface is illuminated with the laser beam, wherein the third image is a second reference image.

The method can further include removing the illumination of the surface by the laser beam during the decreasing of the vacuum pressure applied to the surface from the first vacuum pressure to the second vacuum pressure, and comparing the first inspection image with the first reference image to detect differences between the first inspection image and the first reference image that would indicate workpiece defects. Additionally, the method can further include detecting differences between the first inspection image and the first reference image, wherein the differences between the first inspection image and the first reference image indicate debonding of a first workpiece layer from a second workpiece layer.

In an implementation, the increasing of the vacuum pressure from the atmospheric pressure to the first vacuum pressure includes moving a piston to increase a volume of a vacuum chamber and to increase a chamber vacuum pressure within the chamber and opening a valve in fluid communication with the vacuum chamber and the surface of the workpiece. The decreasing of the vacuum pressure from the first vacuum pressure to the second vacuum pressure can include moving the piston to decrease the volume of the vacuum chamber and to decrease the chamber vacuum pressure within the chamber and opening the valve in fluid communication with the vacuum chamber and the surface of the workpiece.

In an implementation, the valve can be a first solenoid pneumatic valve, and the method can further include moving a second solenoid pneumatic valve in fluid communication with the vacuum chamber from a closed position to an open position and injecting a gas into the vacuum chamber through the second solenoid pneumatic valve in the open position.

The increasing of the vacuum pressure applied to the surface of the workpiece from the atmospheric pressure to the first vacuum pressure can include moving a piston to increase a chamber volume of a vacuum chamber of the vacuum system and to increase a chamber vacuum pressure within the vacuum chamber. The decreasing of the vacuum pressure applied to the surface of the workpiece from the first vacuum pressure to the second vacuum pressure can include moving the piston to decrease the chamber volume of the vacuum chamber and to decrease the chamber vacuum pressure within the vacuum chamber. The increasing of the vacuum pressure applied to the surface of the workpiece from the second vacuum pressure to the third vacuum pressure can include moving the piston to increase the chamber volume of the vacuum chamber and to increase the chamber vacuum pressure within the vacuum chamber. The increasing of the vacuum pressure from the atmospheric pressure to the first vacuum pressure, the decreasing of the vacuum pressure from the first vacuum pressure to the second vacuum pressure, and the increasing of the vacuum pressure from the second vacuum pressure to the third vacuum pressure is performed at a frequency of at least 60 hertz. In an implementation, the second vacuum pressure can be from ¼ to ¾ of the first vacuum pressure.

BRIEF DESCRIPTION OF THE DRAWINGS

The accompanying drawings, which are incorporated in, and constitute a part of this specification, illustrate implementations of the present teachings and, together with the description, serve to explain the principles of the disclosure. In the figures.

Figure 1:
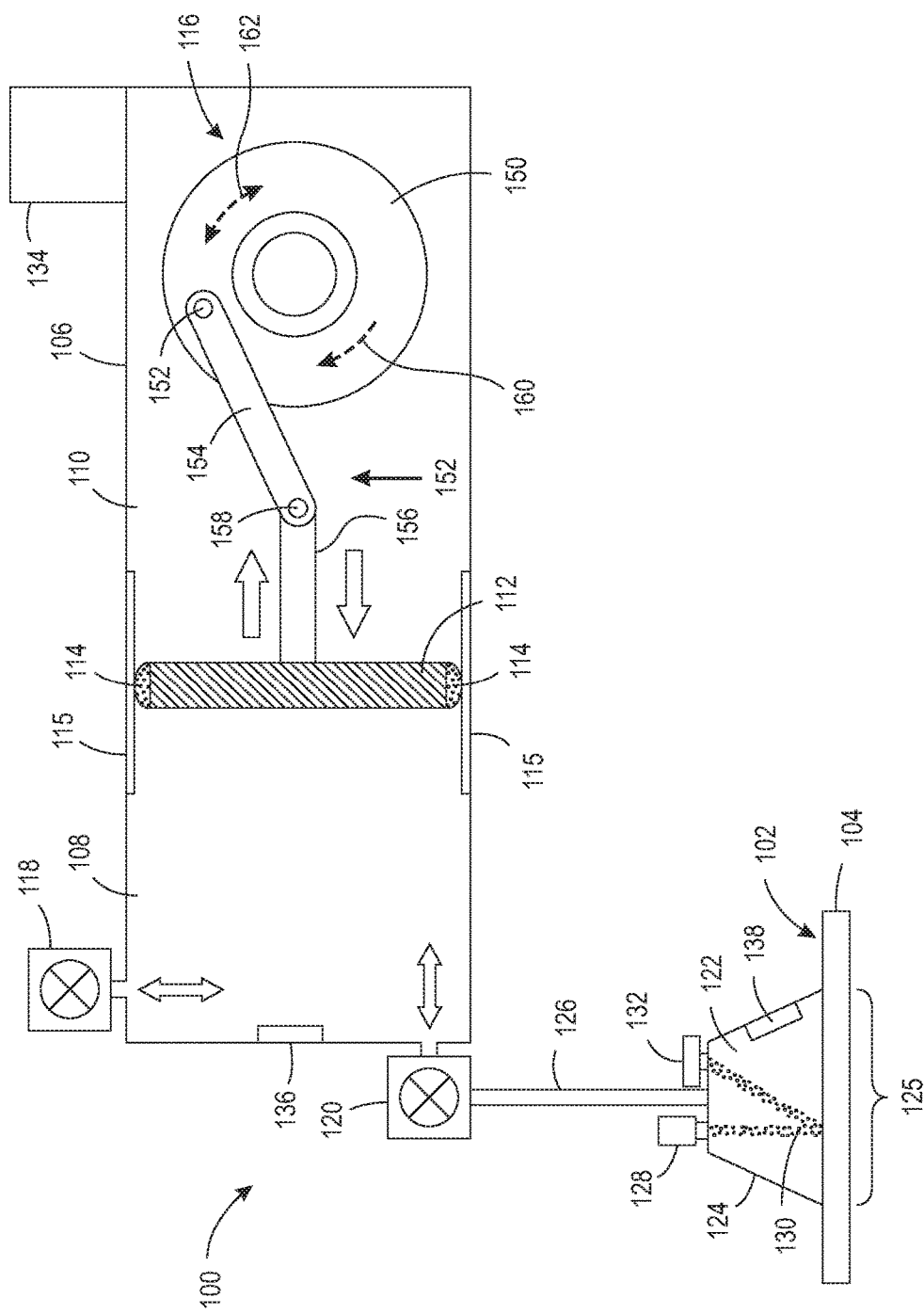
FIG. 1 is a sectional side view of a vacuum system in accordance with an implementation of the present teachings.

It should be noted that some details of the figures have been simplified and are drawn to facilitate understanding of the present teachings rather than to maintain strict structural accuracy, detail, and scale.

DETAILED DESCRIPTION

Reference will now be made in detail to exemplary implementations of the present teachings, examples of which are illustrated in the accompanying drawings. Wherever possible, the same reference numbers will be used throughout the drawings to refer to the same or like parts.

As used herein, "atmospheric pressure" refers to the natural pressure exerted by the weight of the air in the Earth's atmosphere and, for simplicity of explanation, is assumed to be standard pressure (760 Torr). The phrase "vacuum pressure" refers to a negative pressure artificially exerted on or at a surface or other structure by a vacuum system, where the vacuum pressure is less than atmospheric pressure (e.g., a pressure of less than 760 Torr). As used herein, no vacuum pressure exists at atmospheric pressure (~760 Torr), and vacuum pressure increases to a theoretical maximum of a perfect vacuum at 0 Torr.

As discussed above, industries employ vacuum systems for uses such as testing and inspection. For example, shearography is an inspection technique that can be employed to detect defects within a laminated structure such as a decorative laminate. These laminated structures can be used, for example, in aircraft interiors that undergo pressure changes during pressurization of the aircraft interior prior to ascending and/or pressure changes that occur while the aircraft is ascending and descending. Decorative laminate can include a decorative outer layer attached to a porous inner honeycomb core with an adhesive layer. During pressure changes within the aircraft during pressurization or altitude changes, structural defects such as delamination and debonding of the laminate can result in surface flaws. Propensity of laminates to exhibit these surface flaws can be identified using shearography, which can include a vacuum stress (i.e., a vacuum pressure) applied to the surface of the structure. During the application of the vacuum stress, the surface is illuminated with coherent light to create an interference pattern (i.e., speckle pattern) as known in the art of laser interferometry. The coherent light may be from a laser or another source of coherent light where, as known in the art of laser technology, coherent light includes monochromatic light in which electromagnetic waves maintain a fixed and predictable phase relationship with each other over a period of time. The illuminated surface is imaged, typically using a charge coupled device (CCD), to provide an inspection image (i.e., test image or subtract image) that is compared to a reference image of the surface typically by subtracting the inspection image from the reference image, where the reference image is obtained in the absence of the vacuum stress at atmospheric pressure. As the reference image is obtained by imaging the surface under inspection itself, this inspection method is less susceptible to error from decorrelation noise (i.e., "D-noise") than some other inspection techniques.

During conventional shearography, the reference image is obtained while the surface is exposed to atmospheric pressure, a vacuum pressure is applied to the surface using a shearography hood, an inspection image is obtained, and the vacuum pressure is removed which again exposes the surface to atmospheric pressure. This cycle can be repeated, where the vacuum pressure applied to the surface is the same or different than previous cycles. However, between each vacuum pressure application the surface is returned to atmospheric pressure, which is a limitation of conventional vacuum system designs.

A vacuum system according to an implementation of the present teachings can be used to apply a series of vacuum pressures to the surface of a test sample, wherein the series can include a vacuum profile not available with conventional vacuum systems. Different vacuum profiles can improve the identification of defects. Furthermore, the vacuum system according to the present teachings can apply the series of vacuum pressures at a rapid cycle rate, for example, a frequency of from about 0.1 hertz (Hz) to about 1000 Hz, for example about 60 Hz or greater, or from about 60 Hz to about 1000 Hz. Conventional systems used for shearography operate to maintain a constant vacuum pressure on a surface for one minute or longer. These prior systems include digitally controlled release valves that do not operate at high speeds and are not required to operate at high speeds. Operating digitally controlled release valves at high speeds of from, for example, 60 Hz to 1000 Hz would result in operational failure of the digitally controlled release valves. In contrast, a vacuum system in accordance with the present teachings can include the use of solenoid pneumatic valves and can therefore operate across a range of 0.1 Hz to 1000 Hz, or from 60 Hz or greater, for an extended period of time without failure, which are not used in conventional systems that are not required to perform at high operational frequencies. High frequency operation of the vacuum system allows for improved detection of some defects found in, for example, laminated structures. Higher frequency operation may improve, for example, imaging consistency, and D-noise may be thereby reduced compared to systems operating at a lower range of operational frequencies.

In one implementation of the present teachings, the vacuum system can be designed such that the vacuum pressures applied to the surface of the test sample can be increased and decreased without returning the test sample surface to atmospheric pressure. Obtaining reference images at an elevated vacuum pressure without returning to atmospheric pressure results in a different baseline than reference images obtained at atmospheric pressure, and aids in decreasing D-noise. For example, in an implementation, a first reference image can be obtained from the surface of the test sample at atmospheric pressure. Subsequently, a first vacuum pressure can be applied to the surface of the test sample, a first inspection image is obtained at the first vacuum pressure, the vacuum pressure applied to the surface can be decreased to a second vacuum pressure that is lower than the first vacuum pressure, but higher than atmospheric pressure. A second reference image is obtained from the test sample surface at the second vacuum pressure, and the vacuum pressure applied to the test sample surface can be increased to a third vacuum pressure that is higher than the first vacuum pressure, without returning the sample to atmospheric pressure. Thus the mean vacuum pressure applied to the test sample surface can continually increase over time without returning the test sample surface to atmospheric pressure until the inspection, or a portion of the inspection, has been completed.

FIG. 1 is a schematic cross section depicting an interior of a vacuum system 100 according to an implementation of the present teachings. The vacuum system 100 can be operated to perform testing and/or inspection on a surface 102 of a workpiece 104, such as a laminated workpiece 104. The workpiece 104 can be, for example, a decorative laminate as described above.

The vacuum system 100 of FIG. 1 includes a housing 106 that at least partially defines a vacuum chamber 108 and a driver chamber 110, and a piston 112 that generally separates the vacuum chamber 108 from the driver chamber 110. One or more seals 114 can be positioned between the piston 112 and the housing 106 to reduce or prevent the passage of air around the piston 112 such that a vacuum pressure can be generated and maintained within the vacuum chamber 108. Each seal 114 can physically contact a low-friction liner 115 that reduces wear of the seal 114 during movement of the piston 112. A driver 116 such as an electromechanical driver 116 positioned within the driver chamber 110 is mechanically coupled to the piston 112 and configured to move or oscillate the piston 112 back and forth within the housing 106, thereby increasing and decreasing a chamber volume of the vacuum chamber 108.

The vacuum chamber 108 further includes a first valve 118 and a second valve 120, both of which are in fluid communication with the vacuum chamber 108. Each of the two valves 118, 120 can be selectively positioned in a first position to allow an intake or an exhaust of air into the vacuum chamber 108, or a second closed position to prevent either the intake or exhaust of air into or out of the vacuum chamber 108, depending on an operational mode of the vacuum system 100 as described herein.

The first valve 118 can be positioned to selectively allow or prevent a flow of environmental air or another gas from a supplied gas source into and out of the vacuum chamber 108. The second valve 120 is in fluid communication with a test chamber 122 which, in the depicted implementation, is defined at least in part by a hood 124 such as a vacuum shearography hood 124 and a test area 125 of the workpiece 104. Fluid communication between the vacuum chamber 108 and the hood 124 through the second valve 120 can be provide by a flexible hose or tube 126 connected to the hood 124 and the second valve 120. In an aspect of this implementation, the surface 102 of the workpiece 104, specifically the surface 102 of the test area 125, are in fluid communication with the atmosphere through the test chamber 122, the flexible hose 126, the second valve 120, the vacuum chamber 108, and the first valve 118.

The vacuum system 100 can further include a laser 128 configured to output a laser beam 130 and a camera 132. The laser 128 and the camera 132 can be attached to the hood 124. The hood 124 can include other features which have not been depicted for simplicity, such as various tilt mirrors and/or optical deflectors which, for example, deflect the laser beam 130 to allow imaging of the laser beam 130 by the camera 132 to form the inspection image (speckle pattern, interference pattern) during testing or inspection.

The position and/or operation of the first valve 118 and the second valve 120, and the operation of each of the driver 116 which moves and positions the piston 112, the laser 128, the camera 132, and other electrical and mechanical structures of the vacuum system 100 can be controlled and/or monitored by a direct encoder drive (i.e., controller) 134. The controller 134 can be in wired, wireless, electrical, mechanical, electromechanical, electromagnetic, etc., communication with each of the driver 116, the first valve 118, the second valve 120, the laser 128, the camera 132, and other structures and subcomponents of the vacuum system 100. The vacuum system 100 can include other structures that are monitored and/or controlled by the controller 134, for example, one or more pressure sensors 136 positioned within the vacuum chamber 108, one or more pressure sensors 138 positioned on the hood 124 and within the test chamber 122.

The movement or operation of the driver 116 positions the piston 112 within the housing 106 which, in turn, controls the volume of the vacuum chamber 108. The volume of the vacuum chamber 108 increases as the piston 112 moves toward the driver 116 and decreases as the piston 112 moves away from the driver 116. If the first valve 118 is in the closed position and either the second valve 120 is in the closed position or the hood 124 is sealed against the surface 102 of the workpiece 104, or both, the vacuum pressure within the vacuum chamber 108 increases as the piston 112 moves toward the driver 116 and decreases as the piston 112 moves away from the driver 116. When the first valve 118 is in the closed position, the second valve 120 is in the open position, and the hood 124 is sealed against the surface 102 of the workpiece 104, the vacuum pressure within the test chamber 122 increases as the piston 112 moves toward the driver 116 and decreases as the piston 112 moves away from the driver 116. Opening the first valve 118 equalizes the pressure within the vacuum chamber 108 with atmospheric pressure. Opening the second valve 120 equalizes the pressure within the test chamber 122 to the pressure within the vacuum chamber 108.

The first valve 118 and the second valve 120 can be high-speed valves. In an implementation, each of the two valves 118, 120 can be configured independently for switching between the open position and the closed position at a rate of 30 times per second or greater, for example, at a rate of 60 times per second or greater. The two valves 118, 120 can be solenoid pneumatic valves, for example, a model PA07 high speed dispensing valve available from TLX Technologies of Pewaukee, Wis., or another suitable valve.

As depicted in the FIG. 1 implementation, the driver 116 includes a rotatable drive wheel 150 and a crank 152 that attaches the drive wheel 150 to a first end of a connecting rod 154. The connecting rod 154 is attached at a second end to a piston rod 156 using, for example, an end link 158. The piston rod 156 can be fixed to, formed as a part of, or integral with, the piston 112. Other types of drivers or driving mechanisms are contemplated, for example, electromechanical drivers, electromagnetic drivers, mechanical drivers, etc.

Movement of the piston 112 and thus the volume of the vacuum chamber 108 are controlled by the movement of the drive wheel 150, with the movement of the drive wheel 150 controlled by the controller 134. The drive wheel 150 can rotate at a continuous speed or at a variable speed in a single direction as depicted at 160. In another implementation, the drive wheel 150 can rotate in either direction as depicted at 162, which can allow for more varied control of the movement of the piston 112 and the volume of the vacuum chamber 108 compared to the implementation of 160 which can operate at a constant or variable rotational speed.

The controller 134 thus controls and coordinates operation of the driver 116, the first valve 118, the second valve 120, the laser 128, and the camera 132. Operation of the controller 134 can be directed through software and/or firmware instructions stored within memory (not depicted for simplicity). The controller 134 can include electronics, for example, integrated circuits including one or more logic devices such as one or more microprocessors on one or more controller boards (not depicted for simplicity).

Figure 2:
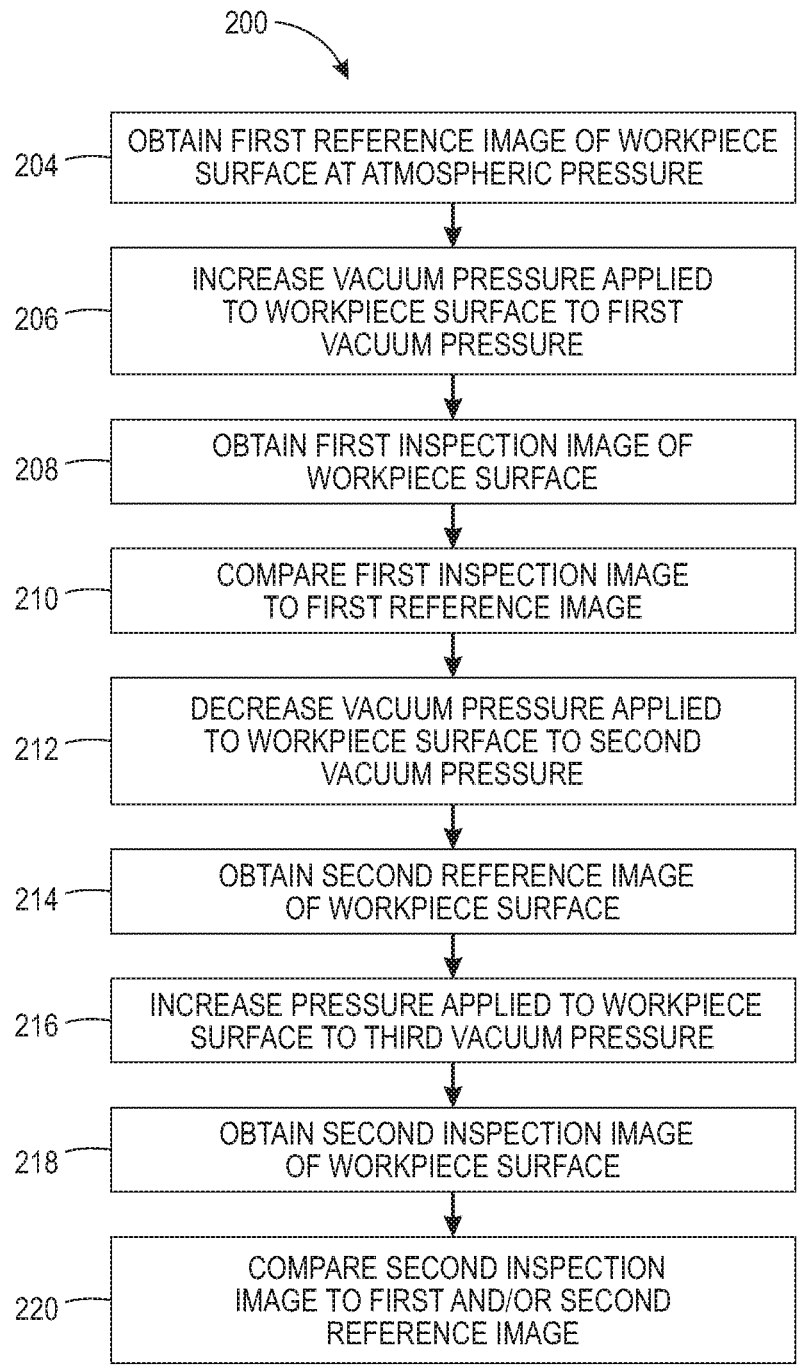
FIG. 2 is a flow diagram of a process for inspecting a workpiece such as a decorative laminate that can be performed using a vacuum system in accordance with the present teachings.

One example method 200 for inspecting a workpiece using a vacuum system is depicted in the flow chart or flow diagram of FIG. 2. The method 200 can proceed by operation or use of one or more of the structures depicted in FIG. 1 described above, and thus is described with reference to FIG. 1; however, it will be appreciated that the method 200 is not limited to any particular structure or use unless expressly stated herein.

As depicted at 204, a first reference image of the workpiece surface 102, specifically the surface 102 of the test area 125, at atmospheric pressure is obtained. To obtain the first reference image, the hood 124 can be placed onto the surface 102 of the workpiece 104 to form the test chamber 122. The first valve 118 and the second valve 120 can both be opened, if not already open. The pressure within the test chamber 122 is at atmospheric pressure (e.g., 760 Torr, 0 vacuum pressure) and the piston 112 can be positioned at a maximum distance from the driver 116 such that the volume of the vacuum chamber 108 is at a minimum permitted by the design of the vacuum system 100, which can vary according to the design and use of the vacuum system. A vacuum system in accordance with an implementation of the present teachings can be relatively compact and portable, while allowing a wide range of vacuum pressures at a high range of operational frequencies, for example from about 0.1 cycles per second (i.e., Hz) to 1000 Hz, or from about 60 Hz to about 1000 Hz, or at least 60 Hz or greater, to be applied to the test structure. As discussed above, high frequency operation of the vacuum system allows for improved detection of some defects found in, for example, laminated structures. Higher frequency operation may improve, for example, imaging consistency, and D-noise may be thereby reduced compared to systems operating at a lower range of operational frequencies. The driver 116, in cooperation with the other vacuum system elements, can enable cycling of the piston 112 from a first position that configures the chamber volume of the vacuum chamber 108 at the maximum, to a second position that configures the chamber volume of the vacuum chamber 108 to the minimum, and back to the first position at a frequency of at least 60 hertz.

With the surface 102 at atmospheric pressure, the controller 134 can switch on (i.e., enable) the laser 128 to illuminate the surface 102 with the laser beam 130. While the surface 102 is illuminated, the controller triggers the camera 132 to image the laser beam 130 reflected from the surface 102 of the workpiece 104, thereby providing the first reference image as at 204, where the first reference image includes a speckle pattern which can be processed to provide a data set that can be stored in memory.

Next, the first valve 118 can be closed and the piston 112 can be moved toward the driver 116 to increase the volume of the vacuum chamber 108, which increases the vacuum pressure within the vacuum chamber 108 to a first vacuum pressure. As the second valve 120 is open, the first vacuum pressure is also applied to the surface 102 of the test area 125 of the workpiece 104 as at 206. While the first vacuum pressure is applied to the surface 102, and while illuminating the surface 102 with the laser beam 130, the controller triggers the camera 132 to image the laser beam 130 reflected from the surface 102 of the workpiece 104, thereby providing a first inspection image of the surface 102 of the workpiece 104 as at 208, including a speckle pattern, which is stored in memory. After obtaining the first inspection image, the laser 128 can be disabled.

The first reference image and the first inspection image are processed and/or analyzed by the controller 134 or another processor and converted to data such as digital data. The first inspection image (i.e., the first inspection image digital data) is compared to the first reference image (i.e., the first reference image digital data), for example, by subtracting the first inspection image from the first reference image, to detect differences between the first inspection image and the first reference image as at 210. When detected, the differences indicate workpiece defects, for example, delamination or debonding of a first layer from a second layer. The defect can result from, for example, failure of an adhesive layer between the first and second layers, gas pockets between the first and second layers formed during manufacture of the workpiece, fracture of a layer, or other failure modes.

Next, the piston 112 is moved away from the driver 116 to decrease the volume of the vacuum chamber 108, which also decreases the vacuum pressure within the vacuum chamber 108 and the vacuum pressure applied to the workpiece surface 102 to a second vacuum pressure as at 212. The second vacuum pressure can be more than atmospheric pressure but less than the first vacuum pressure. While the second vacuum pressure is applied to the surface 102, the controller 134 can enable the laser 128 to illuminate the surface 102 with the laser beam 130. While the surface 102 is illuminated, the controller triggers the camera 132 to image the laser beam 130 reflected from the surface 102 of the workpiece 104, thereby providing a second reference image including a speckle pattern as at 214, which is stored in memory. After obtaining the second reference image, the laser 128 can be disabled, for example, to reduce or eliminate D-noise. The second reference image can be processed and/or analyzed to provide a second reference image data set.

The process can continue, for example, by moving the piston 112 toward the driver 116, thereby increasing the volume of the vacuum chamber 108 and the vacuum pressure within the vacuum chamber 108 to a third vacuum pressure. This also applies the third vacuum pressure to the surface 102 of the workpiece 104 as at 218. The third vacuum pressure can be greater than the first vacuum pressure. While applying the third vacuum pressure to the surface 102, a second inspection image of the surface 102 is obtained as at 218. The second inspection image can be, for example, subtracted from the first reference image, the second reference image, and/or the first inspection image during image processing to detect defects in the workpiece such as delamination of two or more layers and fracturing of a layer that results in separation of the laminated layers of the workpiece. These defects result in the workpiece surface having different surface contours while undergoing different loads at different vacuum pressures applied to the surface by the vacuum system.

It will be understood that while a second image that includes a second speckle pattern may be subtracted from a first image that includes a first speckle pattern during image processing to detect defects in the workpiece, or another comparison technique may be employed to detect defects in the workpiece, defects may not be present and thus defects may not be detected or identified. It will be further understood that the method described herein is merely one example of a process that can be performed using a vacuum system in accordance with the present teachings.

Figure 3:
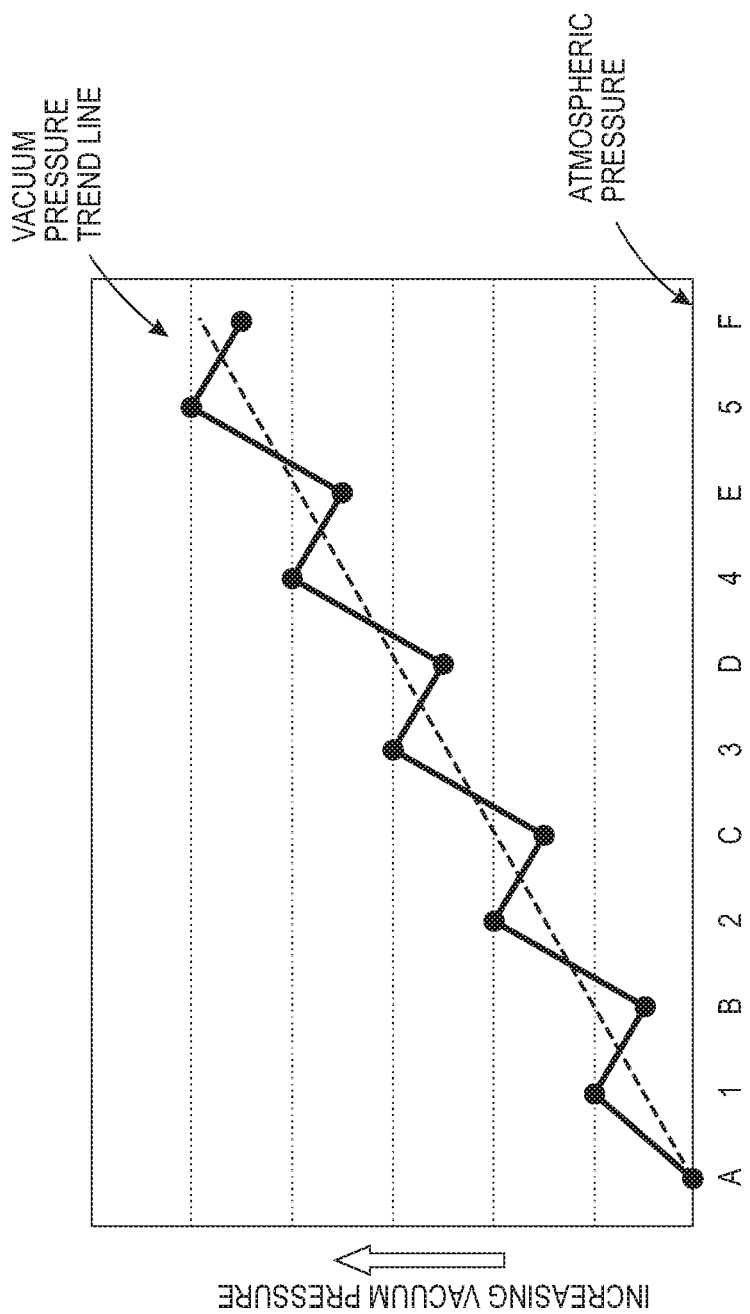
FIG. 3 is graph depicting an example vacuum pressure profile that can be applied to a surface of a workpiece using a vacuum system in accordance with an implementation of the present teachings.

FIG. 3 depicts an example vacuum profile that can be performed using the vacuum system 100 as described herein. As depicted in this implementation, reference images are identified by letters A-F, while inspection images are identified by numbers 1-5. The plurality of reference images B-F and inspection images 1-5 are obtained during the application of alternating increased and decreased vacuum pressures that are applied to the surface 102 of the test area 125 without returning the surface 102 of the test area 125 to atmospheric pressure. As depicted, the vacuum pressure trend line in this implementation generally increases linearly. It will be appreciated that the pressures identified at A-F and 1-5 may be held for a period of time during, or to allow, imaging of the test surface, or the process may be performed using the timing depicted.

In an implementation, after applying an increased vacuum pressure to the surface 102 of the workpiece 104 (e.g., vacuum pressure for inspection images 1-5), the vacuum pressure can be reduced or decreased for the next succeeding reference image B-F. For example, the vacuum pressure value used at inspection images 1-5 can be reduced by about ¼ to about ¾, or by about ⅓ to about ⅔, or by about 30% to about 70%, or by about ½, or any decreased pressure value (without first decreasing the vacuum pressure to atmospheric pressure) to result in the vacuum pressure for the immediately succeeding reference image B-F.

As discussed above, the first valve 118 and the second valve 120 can be high-speed valves such as solenoid pneumatic valves. These high-speed valves, when used in conjunction with the piston 112 as described above, assists in the enablement of a rapid, controlled, and accurate change of vacuum pressure within the vacuum chamber 108 and the test chamber 122 compared to conventional vacuum systems. Further, the laser 128 can be switched off during these pressure changes, for example to reduce D-noise, and the camera 132 obtains inspection images only when the laser 128 is enabled. Camera data can be transferred and processed during these camera downtimes, which also assists to enable rapid vacuum system cycling. In an implementation, one complete inspection cycle includes three successive inspection images, and the vacuum system described herein can operate at a frequency of at least 60 hertz (i.e., ≥60 inspection cycles per second).

It will be understood that the vacuum profile of FIG. 3 is merely one example vacuum profile that can be performed by, and obtained with, a vacuum system in accordance with an implementation of the present teachings. Further, it will be appreciated that a vacuum system in accordance with the present teachings can include structures that, for clarity and simplicity, have not been depicted in the figures, and that various depicted structures can be removed or modified. For example, it is contemplated that a vacuum system can be used as a standalone system without inspection subsystems, or can include inspection subsystems other than, or in addition to, laser shearography, such as acoustic shearography or inspection subsystems other than those that employ the use of shearography. With regard to FIG. 3 and one aspect of this disclosure, one cycle can be defined as operation of the vacuum system that includes three successive images, where FIG. 3 depicts five complete cycles of operation.

Figure 4:
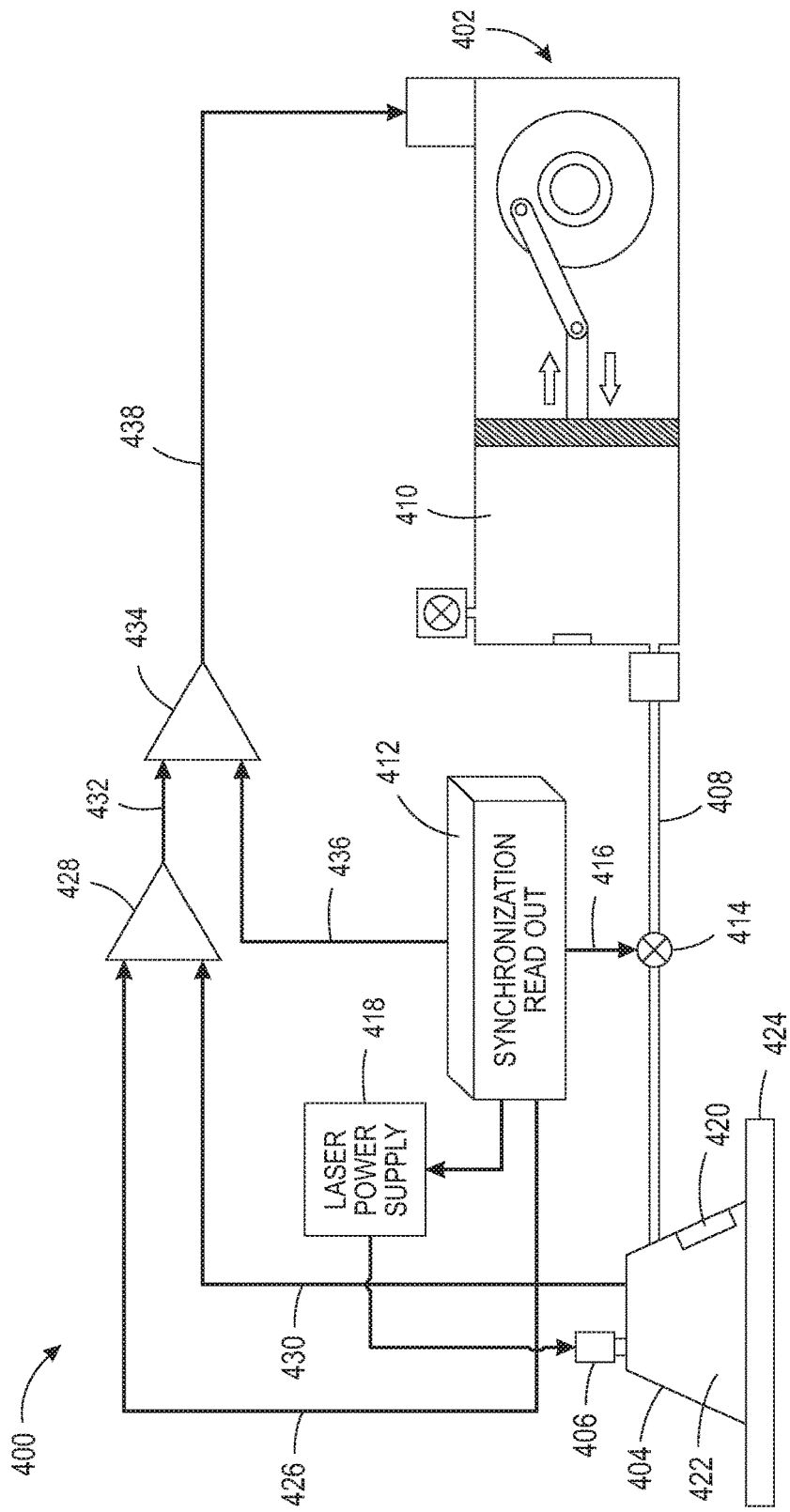
FIG. 4 is a schematic depiction of a vacuum system including supporting electronics in accordance with an implementation of the present teachings.

FIG. 4 is a schematic depiction of a shearography system 400 in accordance with an implementation of the present teachings. The shearography system 400 can include a vacuum system 402, a hood 404, a laser 406, and a hose 408 that can be the same or different than those described above with reference to FIG. 1. The hose 408, at least in part, establishes fluid communication between a vacuum chamber 410 of the vacuum system 402 and the hood 404. The shearography system 400 includes a synchronization read out or synchronizer 412 that can be, include, or function cooperatively with the controller 134 of FIG. 1, which monitors and/or controls other subsystems of the shearography system 400. The synchronizer 412 controls operation of a synch valve 414 that opens to allow air to flow between the vacuum chamber 410 and the hood 404 and closes to prevent air from flowing between the vacuum chamber 410 and the hood 404. The synch valve 414 can be a solid state actuator, for example, a solenoid pneumatic valve controlled by the synchronizer 412 using a connection 416 such as an electrical connection 416. The synchronizer 412 further controls operation of the laser 406, for example, through connection to a laser power supply 418.

During operation, the shearography system 400 can compare a desired vacuum pressure within the hood 404 to an actual vacuum pressure measured using a pressure sensor 420. The synchronizer 412 can then control operation of various other shearography system components to regulate vacuum pressure within the hood 404 (i.e., within a test chamber 422 formed by the hood 404 and a workpiece 424). For example, the synchronizer 412 can output a first signal 426 identifying a desired vacuum pressure to a first comparator 428, which also receives a second signal 430 identifying the actual vacuum pressure from the pressure sensor 420. Output 432 from the first comparator 428 is input as a third signal 432 to a second comparator 434, which also receives a fourth signal 436 from the synchronizer 412 identifying total pressure. The fourth signal 436 can provide a vacuum limiter to ensure that the vacuum pressure applied to the test surface does not exceed a maximum value. Output 438 from the second comparator 434 is input as a fifth signal 438 to the vacuum system 402, thereby controlling operation of a vacuum system driver 440 (for example, the driver 116 of FIG. 1).

Figure 5:
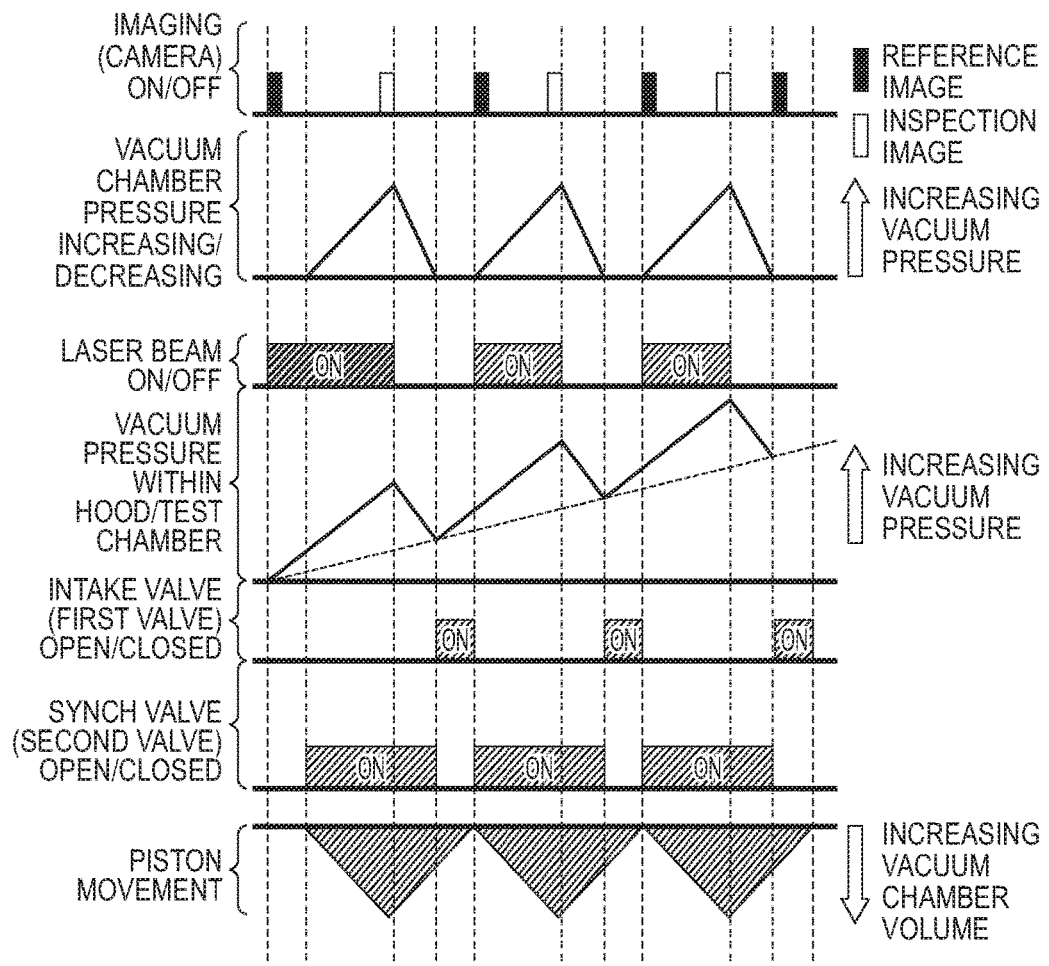
FIG. 5 is a timing diagram depicting cooperative functionality of various vacuum system components in an example implementation of the present teachings.

FIG. 5 is a timing diagram depicting timing of various components of a shearography system according to an example implementation of the present teachings. It will be understood that other component timing and additional components are contemplated, and that various components included in FIG. 5 can be removed or modified. While FIG. 5 is described with reference to FIGS. 1 and 4, it will be understood that other vacuum systems in accordance with the present teachings are contemplated.

In FIG. 5, images are captured by a camera 132, for example, when the laser 128/406 is activated (i.e., when the laser beam 130 is on). The images include reference images and inspection images. The inspection images can be compared to (e.g., subtracted from) the one or more of the reference images and/or from other inspection images.

In FIG. 5, vacuum pressure within the vacuum chamber 108/410 increases and decreases, depending on the timing of the piston 112, the intake valve (i.e., first valve) 118, and the synch valve (i.e., second valve) 120/414. Further, the laser beam 130 is controlled to be on during image capture and off when no image is to be captured. The timing of the camera 132 is thus coordinated with the activation and deactivation of the laser 128/406.

In FIG. 5, the vacuum pressure within the hood 124/404 and/or test chamber 122/422 begins at atmospheric pressure, at which point the first reference image can be captured. The vacuum pressure then increases and decreases without returning to atmospheric pressure.

The operation of the intake valve (i.e., first valve) 118 is coordinated with the operation of the synch valve (i.e., second valve) 120/414. In the timing diagram of FIG. 5, the synch valve 120/414 is open only when the intake valve 118 is closed. This ensures that vacuum pressure within the hood 124/404 and/or test chamber 122/422 does not decrease as a direct result of air entering the intake valve 118. As depicted, the vacuum pressure within the hood 124/404 and/or test chamber 122/422 can decrease as a direct result of the piston 112 moving away from the driver 116 and decreasing a volume of the vacuum chamber 108/410.

Figure 6:
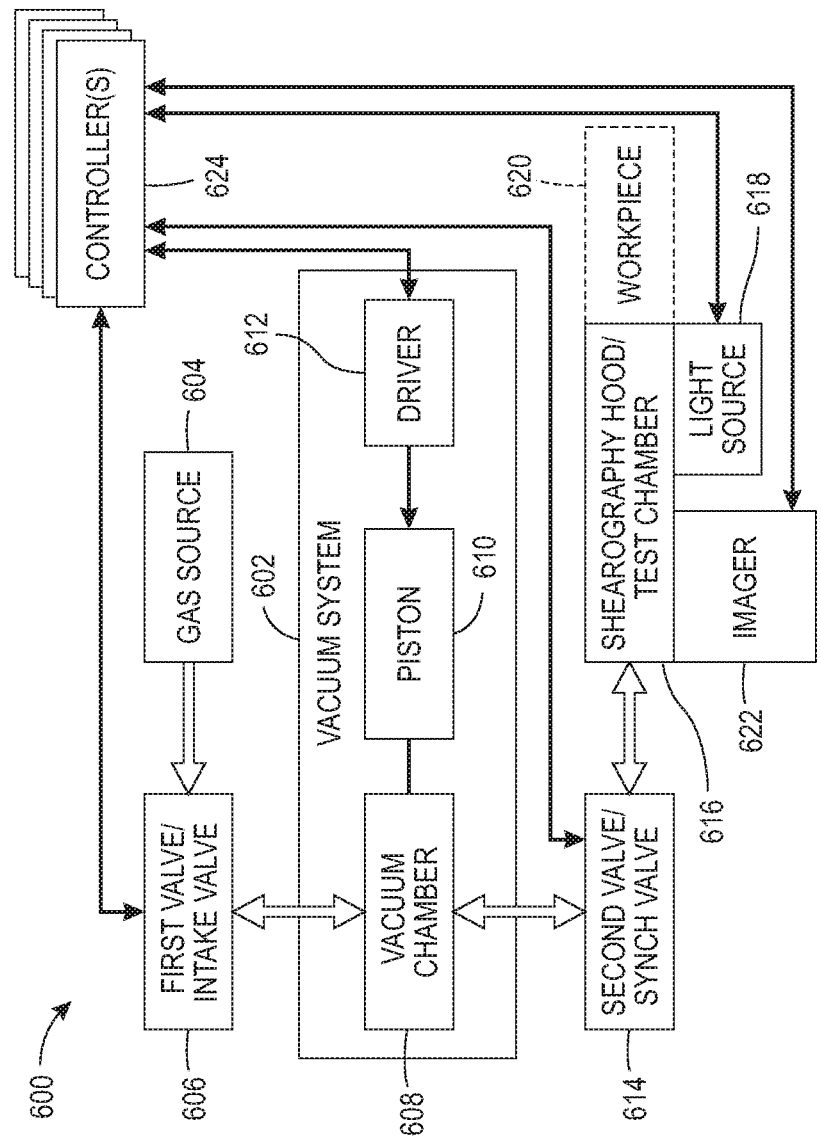
FIG. 6 is a functional block diagram of a shearography system which uses a vacuum system in accordance with the present teachings.

FIG. 6 is a functional block diagram of a shearography system 600 which uses a vacuum system 602 in accordance with an implementation of the present teachings. As depicted in FIG. 6, the shearography system 600 includes a gas source 604 which can be or include ambient air from the atmosphere, a gas source from a gas supply or gas canister, or a combination of gas sources. The shearography system 600 further includes a first valve (e.g., intake valve) 606 in fluid communication with the gas source 604. The first valve 606 is in fluid communication with a vacuum chamber 608 of the vacuum system 604. A volume of the vacuum chamber 608 increases and decreases relative to movement of a piston 610, where the movement of the piston 610 is controlled by a driver 612. The vacuum chamber 608 is further in fluid communication with a second valve (e.g., synch valve 614), such that the second valve 614 is in fluid communication with the gas source 604 through the vacuum chamber 608 and through the first intake valve 606. The second valve 614 is in fluid communication with a shearography hood (e.g., test chamber) 616, and the flow of gas through the second valve 614 thus at least partly determines the flow of gas into and out of the shearography hood 616, and the vacuum pressure within the shearography hood 616. A light source 618 such as a laser is configured to illuminate a workpiece 620 (depicted in phantom as not being part of the shearography system 600 itself) with light such as a laser beam while a pressure or a series of pressures, for example, atmospheric pressure and/or one or more vacuum pressures, are applied to the workpiece 620 at or within the shearography hood 616. An imager 622 such as a camera that may include a CCD device is configured to image the workpiece 620 at atmospheric pressure and during the application of the one or series of pressures to the workpiece 620 and to obtain one or more reference images and/or one or more inspection images of the workpiece 620. In an implementation, the inspection image may be subtracted from the reference image to detect defects such as delamination or other separation of workpiece lamination layers. Each of the first intake valve 606, the driver 612, the second valve 614, the light source 618, and the imager 622 may be controlled and/or monitored by one or more controllers 624. The shearography system 600 may include other structures not depicted for simplicity, such as pressure sensors to monitor pressures at various locations, with pressure data from the sensor being received by the controllers 624 which thereby monitor and control pressures within the various subcomponents. The shearography system 600 may thus apply a pressure or series of different pressures to the workpiece 620 and image the workpiece 620 during the application of pressure(s).

Some or all of the disclosed method can thereby be advantageously automated. For example, the increase and decrease of vacuum pressure can be accomplished without an operator by using a computer to control the change in vacuum pressures. This allows inspection to proceed at an accelerated rate so a larger area can be inspected compared to methods reliant on an operator. Automation can further include the determining whether a defect exists by using image processing and pattern recognition software. This can avoid the need for a trained technician to perform the inspection and increase consistency of results.

Notwithstanding that the numerical ranges and parameters setting forth the broad scope of the present teachings are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less than 10" can assume negative values, e.g., −1, −2, −3, −10, −20, −30, etc.

While the present teachings have been illustrated with respect to one or more implementations, alterations and/or modifications can be made to the illustrated examples without departing from the spirit and scope of the appended claims. For example, it will be appreciated that while the process is described as a series of acts or events, the present teachings are not limited by the ordering of such acts or events. Some acts can occur in different orders and/or concurrently with other acts or events apart from those described herein. Also, not all process stages can be required to implement a methodology in accordance with one or more aspects or implementations of the present teachings. It will be appreciated that structural components and/or processing stages can be added or existing structural components and/or processing stages can be removed or modified. Further, one or more of the acts depicted herein can be carried out in one or more separate acts and/or phases. Furthermore, to the extent that the terms "including," "includes," "having," "has," "with," or variants thereof are used in either the detailed description and the claims, such terms are intended to be inclusive in a manner similar to the term "comprising." The term "at least one of" is used to mean one or more of the listed items can be selected. As used herein, the term "one or more of" with respect to a listing of items such as, for example, A and B, means A alone, B alone, or A and B. Further, in the discussion and claims herein, the term "on" used with respect to two materials, one "on" the other, means at least some contact between the materials, while "over" means the materials are in proximity, but possibly with one or more additional intervening materials such that contact is possible but not required. Neither "on" nor "over" implies any directionality as used herein. The term "conformal" describes a coating material in which angles of the underlying material are preserved by the conformal material. The term "about" indicates that the value listed can be somewhat altered, as long as the alteration does not result in nonconformance of the process or structure to the illustrated implementation. Finally, "exemplary" indicates the description is used as an example, rather than implying that it is an ideal. Other implementations of the present teachings will be apparent to those skilled in the art from consideration of the specification and practice of the disclosure herein. It is intended that the specification and examples be considered as exemplary only, with a true scope and spirit of the present teachings being indicated by the following claims.

Terms of relative position as used in this application are defined based on a plane parallel to the conventional plane or working surface of a workpiece, regardless of the orientation of the workpiece. The term "horizontal" or "lateral" as used in this application is defined as a plane parallel to the conventional plane or working surface of a workpiece, regardless of the orientation of the workpiece. The term "vertical" refers to a direction perpendicular to the horizontal. Terms such as "on," "side" (as in "sidewall"), "higher," "lower," "over," "top," and "under" are defined with respect to the conventional plane or working surface being on the top surface of the workpiece, regardless of the orientation of the workpiece.

The invention claimed is:

1. A vacuum system for inspecting a workpiece, the vacuum system comprising:
   a housing defining at least a portion of a vacuum chamber;
   a piston within the housing, wherein the piston is configured to oscillate, thereby varying a chamber volume of the vacuum chamber;
   a first valve in fluid communication with the vacuum chamber, wherein the first valve comprises a first or open position that permits an intake of a gas into the vacuum chamber and an exhaust of the gas out of the vacuum chamber through the first valve, and a second closed position that prevents an intake of the gas into the vacuum chamber and an exhaust of the gas out of the vacuum chamber through the first valve;

a second valve in fluid communication with the vacuum chamber, wherein the second valve comprises an open position that permits an intake of the gas into the vacuum chamber and an exhaust of the gas out of the vacuum chamber through the second valve, and a closed position that prevents an intake of the gas into the vacuum chamber and an exhaust of the gas out of the vacuum chamber through the second valve; and a hood in fluid communication with the second valve and the vacuum chamber, wherein the second valve, in the open position, permits a flow of the gas between the vacuum chamber and the hood and, in the closed position, prevents a flow of the gas between the vacuum chamber and the hood through the second valve, wherein the piston, the first valve, and the second valve are cooperatively configured to:

increase a vacuum pressure applied to a surface of the workpiece from an atmospheric pressure to a first vacuum pressure; then decrease the vacuum pressure applied to the surface of the workpiece to a second vacuum pressure that is lower than the first vacuum pressure; then increase the vacuum pressure applied to the surface of the workpiece to a third vacuum pressure that is higher than the first vacuum pressure without returning the vacuum pressure applied to the surface of the workpiece to the atmospheric pressure until the inspecting, or a portion of the inspecting, has been completed.

2. The vacuum system of claim 1, further comprising a driver comprising a rotatable drive wheel, wherein:

the rotatable drive wheel is mechanically coupled to the piston; and the vacuum system is further configured to oscillate the piston back and forth, thereby increasing and decreasing the chamber volume of the vacuum chamber.

3. The vacuum system of claim 1, wherein the hood is configured to be positioned on a surface the workpiece during an application of a vacuum force to a surface of the workpiece by the vacuum system during inspecting of the workpiece.

4. The vacuum system of claim 3, further comprising a laser configured to activate and deactivate during inspection of the workpiece wherein, during the activation, the laser emits a laser beam which illuminates the surface of the workpiece.

5. The vacuum system of claim 4 further comprising a camera configured to image the surface of the workpiece during the inspection of the workpiece.

6. The vacuum system of claim 1, wherein at least one of the first valve and the second valve is a solenoid pneumatic valve.

7. The vacuum system of claim 1, wherein the piston is configured to move from a first position in which the chamber volume is a maximum chamber volume, to a second position in which the chamber volume is a minimum chamber volume, and to oscillate between the first and second positions at a frequency range of from 0.1 hertz to 1000 hertz.

8. The vacuum system of claim 1, further comprising:

a driver chamber defined at least in part by the housing; and a driver coupled to the piston, positioned within the driver chamber, and configured to oscillate the piston, wherein the piston separates the driver chamber from the vacuum chamber.

9. A shearography system for inspecting a workpiece, comprising:

a vacuum system comprising:

a housing defining at least a portion of a vacuum chamber;

a piston within the housing, wherein the piston is configured to oscillate, thereby varying a chamber volume of the vacuum chamber;

a first valve in fluid communication with the vacuum chamber, wherein the first valve comprises a first or open position that permits an intake of a gas into the vacuum chamber and an exhaust of the gas out of the vacuum chamber through the first valve, and a second closed position that prevents an intake of the gas into the vacuum chamber and an exhaust of the gas out of the vacuum chamber through the first valve;

a second valve in fluid communication with the vacuum chamber, wherein the second valve comprises an open position that permits an intake of the gas into the vacuum chamber and an exhaust of the gas out of the vacuum chamber through the second valve, and a closed position that prevents an intake of the gas into the vacuum chamber and an exhaust of the gas out of the vacuum chamber through the second valve; and a hood in fluid communication with the second valve and the vacuum chamber, wherein the second solenoid pneumatic valve, in the open position, permits a flow of the gas between the vacuum chamber and the hood and, in the closed position, prevents the flow of the gas between the vacuum chamber and the hood through the second valve;

a laser configured to activate and deactivate during inspecting of the workpiece wherein, during the activation, the laser emits a laser beam which illuminates the workpiece;

a camera configured to image the workpiece during inspecting of the workpiece; and a controller configured to coordinate operation of the vacuum system, the laser, and the camera during inspecting of the workpiece, wherein the piston, the first valve, and the second valve are cooperatively configured to:

increase a vacuum pressure applied to a surface of the workpiece from an atmospheric pressure to a first vacuum pressure; then decrease the vacuum pressure applied to the surface of the workpiece to a second vacuum pressure that is lower than the first vacuum pressure; then increase the vacuum pressure applied to the surface of the workpiece to a third vacuum pressure that is higher than the first vacuum pressure without returning the vacuum pressure applied to the surface of the workpiece to the atmospheric pressure until the inspecting, or a portion of the inspecting, has been completed.

10. The shearography system of claim 9, further comprising a driver comprising a rotatable drive wheel, wherein:

the rotatable drive wheel is mechanically coupled to the piston; and the vacuum system is further configured to oscillate the piston back and forth, thereby increasing and decreasing the chamber volume of the vacuum chamber.

11. The shearography system of claim 9, wherein:

the piston is configured to move from a first position in which the chamber volume is a maximum chamber volume, to a second position in which the chamber volume is a minimum chamber volume, and to oscillate between the first and second positions at a frequency range of from 0.1 hertz to 1000 hertz; and the controller is configured to coordinate operation of the piston during inspecting of the workpiece.

12. The shearography system of claim 9, further comprising:

a driver chamber defined at least in part by the housing; and a driver coupled to the piston, positioned within the driver chamber, and configured to oscillate the piston, wherein the piston separates the driver chamber from the vacuum chamber.

13. A method for inspecting a workpiece, comprising:

obtaining a first image of a surface of the workpiece at atmospheric pressure;

increasing a vacuum pressure applied to the surface of the workpiece from the atmospheric pressure to a first vacuum pressure using a vacuum system;

obtaining a second image of the surface of the workpiece at the first vacuum pressure;

decreasing the vacuum pressure applied to the surface of the workpiece from the first vacuum pressure to a second vacuum pressure that is lower than the first vacuum pressure and higher than the atmospheric pressure without decreasing the vacuum pressure to the atmospheric pressure;

obtaining a third image of the surface of the workpiece at the second vacuum pressure; and increasing the vacuum pressure applied to the surface of the workpiece from the second vacuum pressure to a third vacuum pressure that is higher than the first vacuum pressure without decreasing the vacuum pressure to the atmospheric pressure.

14. The method of claim 13, wherein the first image is a first reference image and the method further comprises:

illuminating the surface of the workpiece using a laser beam output by a laser while the first vacuum pressure is applied to the surface;

performing the obtaining of the second image while the surface is illuminated with the laser beam, wherein the second image is a first inspection image of the surface;

illuminating the surface using the laser beam while the second vacuum pressure is applied to the surface; and performing the obtaining of the third image while the surface is illuminated with the laser beam, wherein the third image is a second reference image.

15. The method of claim 14, further comprising removing the illumination of the surface with the laser beam during the decreasing of the vacuum pressure applied to the surface from the first vacuum pressure to the second vacuum pressure.

16. The method of claim 14, further comprising comparing the first inspection image with the first reference image to detect differences between the first inspection image and the first reference image that would indicate a workpiece defect.

17. The method of claim 16, further comprising detecting differences between the first inspection image and the first reference image, wherein the differences between the first inspection image and the first reference image indicate debonding of a first workpiece layer from a second workpiece layer.

18. The method of claim 13, wherein the increasing of the vacuum pressure from the atmospheric pressure to the first vacuum pressure comprises:

moving a piston to increase a volume of a vacuum chamber and to increase a chamber vacuum pressure within the chamber; and opening a valve in fluid communication with the vacuum chamber and the surface of the workpiece.

19. The method of claim 18, wherein the decreasing of the vacuum pressure from the first vacuum pressure to the second vacuum pressure comprises:

moving the piston to decrease the volume of the vacuum chamber and to decrease the chamber vacuum pressure within the chamber; and opening the valve in fluid communication with the vacuum chamber and the surface of the workpiece.

20. The method of claim 19, wherein the valve is a first valve, and the method further comprises:

moving a second valve in fluid communication with the vacuum chamber from a closed position to an open position; and injecting a gas into the vacuum chamber through the second valve in the open position.

21. The method of claim 13, wherein:

the increasing of the vacuum pressure applied to the surface of the workpiece from the atmospheric pressure to the first vacuum pressure comprises moving a piston to increase a chamber volume of a vacuum chamber of the vacuum system and to increase a chamber vacuum pressure within the vacuum chamber;

the decreasing of the vacuum pressure applied to the surface of the workpiece from the first vacuum pressure to the second vacuum pressure comprises moving the piston to decrease the chamber volume of the vacuum chamber and to decrease the chamber vacuum pressure within the vacuum chamber;

the increasing of the vacuum pressure applied to the surface of the workpiece from the second vacuum pressure to the third vacuum pressure comprises moving the piston to increase the chamber volume of the vacuum chamber and to increase the chamber vacuum pressure within the vacuum chamber; and the increasing of the vacuum pressure from the atmospheric pressure to the first vacuum pressure, the decreasing of the vacuum pressure from the first vacuum pressure to the second vacuum pressure, and the increasing of the vacuum pressure from the second vacuum pressure to the third vacuum pressure is performed at a frequency of at least 60 hertz.

22. The method of claim 13, wherein the second vacuum pressure is from ¼ to ¾ of the first vacuum pressure.

* * * * *